US007238840B2

(12) United States Patent
Botella Asuncion et al.

(10) Patent No.: US 7,238,840 B2
(45) Date of Patent: Jul. 3, 2007

(54) PROCESS FOR THE PRODUCTION OF DIAMINODIPHENYLMETHANE AND ITS HIGHER HOMOLOGUES

(75) Inventors: Pablo Botella Asuncion, Valencia (ES); Joris Karel Peter Bosman, Herselt (BE); Avelino Corma, Valencia (ES); Christopher John Mitchell, Veltem-Beisem (BE)

(73) Assignee: Huntsman International LLC, Salt Lake City, UT (US)

( * ) Notice: Subject to any disclaimer, the term of this patent is extended or adjusted under 35 U.S.C. 154(b) by 499 days.

(21) Appl. No.: 10/947,103

(22) Filed: Sep. 21, 2004

(65) Prior Publication Data
US 2005/0101801 A1    May 12, 2005

Related U.S. Application Data

(63) Continuation-in-part of application No. PCT/EP03/03084, filed on Mar. 25, 2003.

(51) Int. Cl.
C07C 209/78   (2006.01)
C07C 263/10   (2006.01)
(52) U.S. Cl. ...................................... 564/332; 560/338
(58) Field of Classification Search ................ 564/332; 560/338
See application file for complete search history.

(56) References Cited

U.S. PATENT DOCUMENTS

| | | | |
|---|---|---|---|
| 2,683,730 A | 7/1954 | Seeger et al. | |
| 2,950,263 A | 8/1960 | Abbotson et al. | |
| 3,260,751 A | 7/1966 | Powers et al. | |
| 3,277,173 A | 10/1966 | Powers et al. | |
| 3,297,759 A | 1/1967 | Curtiss et al. | |
| 3,362,979 A | 1/1968 | Bentley | |
| 3,476,806 A | 11/1969 | Wolf | |
| 4,039,580 A | 8/1977 | Frulla et al. | |
| 4,039,581 A | 8/1977 | Frulla et al. | |
| 4,294,987 A * | 10/1981 | Prather et al. | 564/331 |
| 5,098,684 A | 3/1992 | Kresge et al. | |
| 5,102,643 A | 4/1992 | Kresge et al. | |
| 5,105,051 A | 4/1992 | Pelrine et al. | |
| 5,134,242 A | 7/1992 | Le et al. | |
| 5,134,243 A | 7/1992 | Bhore et al. | |
| 6,231,751 B1 | 5/2001 | Canos et al. | |
| 6,380,433 B1 | 4/2002 | Perego et al. | |

FOREIGN PATENT DOCUMENTS

| | | |
|---|---|---|
| EP | 1055663 | 11/2000 |
| EP | 1211224 | 6/2002 |
| WO | WP 91/11390 | 8/1991 |
| WO | WO 00/07722 | 2/2000 |

OTHER PUBLICATIONS

Corma et al, "A new material highly active and selective for the epoxidation of olefins with organic hydroperoxides", Chem. Commun., 1999, p. 779-780.
A. Corma et al, "Delaminated zoalite precursors as selective acidic catalysts", Nature 396 (1998), p. 353.
J.S. Beck et al, "A new family of mesoporous molecular sieves prepared with liquid crystal templates" J. Am. Chem. Soc., 114 (1992), p. 10834.
Avelino Corma, "From Microporous to Mesoporous Molecular Sieve Materials and Their use in Catalysis", Chem. Rev., 1997, 97, p. 2373-2419.
T. Yanagisawa et al., "The preparation of alkyltrimethylammonium-kanemite complexes and their conversion to microporous materials" Bull. Chem. Soc. Jpn, 63 (1990), p. 988, Vo.
S. Inagaki et al., "Synthesis of highly ordered mesoporous materials from a layered polysilicate" J. Chem. Soc., Chem. Commun., 680 (1993).
C.T. Kresge et al., "Ordered mesoporous molecular sieves synthesized by a liquid-crystal template mechanism", Nature, 359, 710 (1992), vol. 359.
Stud. Surf. Sci. Catal. "Development of a formation mechanism for M41S materials", 84 (1994), p. 53-60.
Stud. Surf. Sci. Catal. "Synthesis and characterization of highly ordered mesopopous material: FSM-16, from a layered polysilicate", 84 (1994), p. 125-132.
A. Corma et al, "Synthesis of an ultralarge pore titanium silicate isomorphous to MCM-41 and its application as a catalyst for selective oxidation of hydrocarbons", J. Chem.
K. Reddy et al., "Synthesis of mesopourous vanadium silicate molecular sieves", J. Chem. Soc., Chem. Commun. (1994), p. 1059-1060.
M. Twigg et al, "Preparation and properties of ceramic foam catalyst supports", Prep. 6th Int. Symp. Sci. Bases Heterog. Cat. 1, (1994), p. 345-352.
B. Zebib et al, "Delaminated phyllosilicates as high acidic catalyst supports", 13th International congress on Catalysis, Paris 2004.
Corma et al., "High activity of layered zeolite ITQ-2 as catalyst for the hydroxyalkylation . . . ", Microporous and Mesoporous Materials 43, 2001, p. 161-169.

* cited by examiner

*Primary Examiner*—Peter O'Sullivan
(74) *Attorney, Agent, or Firm*—Ron D. Brown; Nicole Graham

(57) ABSTRACT

Method of preparing diaminodiphenylmethane and higher homologues thereof from aniline and formaldehyde in the presence of heterogeneous solid acid catalysts selected from (a) delaminated zeolites and/or (b) metal silicate catalysts having an ordered mesoporous pore structure and/or (c) delaminated phyllosilicates.

4 Claims, No Drawings

PROCESS FOR THE PRODUCTION OF DIAMINODIPHENYLMETHANE AND ITS HIGHER HOMOLOGUES

CROSS-REFERENCE TO RELATED APPLICATIONS

This application is a continuation-in-part of international application PCT/EP03/03084, filed Mar. 25, 2003.

FIELD OF THE INVENTION

This invention relates to a method of preparing diaminodiphenylmethane and higher homologues thereof and to a method of preparing polyisocyanates made therefrom.

BACKGROUND OF THE INVENTION

The preparation of the mixtures of methylene-bridged polyphenyl polyamines (hereafter polymethylene polyphenyl polyamines) containing di(aminophenyl)methanes by condensation of aniline and formaldehyde under aqueous conditions in the presence of strong acids, particularly hydrochloric acid, has been widely described. Illustrative of such processes are those shown in, for example, U.S. Pat. Nos. 2,638,730; 2,950,263; 3,260,751; 3,277,173; 3,297,759 and 3,476,806. Such processes, in one form or another, are widely used commercially to prepare the polyamines in question, which polyamines are employed as intermediates in the preparation of the corresponding isocyanates, i.e. diisocyanatodiphenylmethane and mixtures of polymethylene polyphenyl polyisocyanates. The isocyanates are employed in, the preparation of a variety of polyurethanes, polyisocyanurates and other polymers (both cellular and non-cellular), which can be derived from polyisocyanates.

For many purposes, it is desirable that the diamine content of the above polyamines, and the diisocyanate content of the polyisocyanates derived therefrom, contain a high proportion of 4,4'-isomer. This has been achieved largely by employing proportions of strong acid in the condensation of the aniline and formaldehyde with the aniline present in an amount of at least 2 mole per mole of formaldehyde.

There are a number of reasons why it is undesirable to use these high concentrations of strong acid in the condensation. Thus, the presence of the strong acid, particularly in the later stages of the condensation, which are conducted at elevated temperature, represents a serious corrosion problem involving constant repair and maintenance requirements that contribute significantly to the overhead cost of operation of the manufacturing plants in which such processes are utilized. Alternatively, more expensive equipment may be used. Further, the acid in question has to be neutralized, usually by means of aqueous sodium hydroxide, at the end of the reaction and disposal of the resulting neutral salt solution represents a severe problem because of the vast volumes of such material that are generated.

Processes have been described that eliminate the use of the strong acid catalysts and the necessity to neutralize the reaction products and substitute solid catalysts such as clay, zeolites and diatomaceous earth (see, for example, U.S. Pat. Nos. 3,362,979; 4,039,580; and 4,039,581). However, these processes give rise to products in which the 4,4'-isomer content of the diamine is substantially reduced in favor of the 2,4'-isomer, and, in some cases, the 2,2'-isomer.

We have now surprisingly found that the condensation of aniline with formaldehyde, and the conversion of the condensation product to the desired polyamines, can be effected using specific heterogeneous catalysts without having the above mentioned drawbacks.

SUMMARY OF THE INVENTION

An embodiment of the invention relates to a method of preparing diaminodiphenylmethane and higher homologues thereof. The method comprises the step of condensing aniline and formaldehyde either prior to addition of or in the presence of specific heterogeneous catalysts selected from the class of (a) delaminated zeolites and/or (b) metal silicate catalysts having an ordered mesoporous pore structure and/or (c) delaminated phyllosilicates. Subsequently, the resulting mixture is converted, in the presence of said catalyst(s), substantially to the desired mixture of aromatic primary amines. A mixture of products is produced which includes the diaminodiphenylmethane isomers comprising the 2,2', 2,4', and 4,4' diamine isomers and higher homologues thereof or polymethylene polyphenylamines. The latter are higher molecular weight condensation polymers of the formaldehyde and the aniline and are considered homologues of the simple diaminodiphenylmethane isomers.

Depending upon reaction conditions, amount of catalyst employed, proportions of the reactants, and other variables the proportions of diamines, and higher polyamines present in the final reaction mixture may be widely varied. However, usually the reaction mixture contains at least 10 percent by weight of diamine with the remainder being higher polyamines thereof. More often, the percentage of diamines in the mixture is 50-95 percent and most often ranges from about 70 to about 90 weight percent. Correspondingly, the polymeric products higher than the diamine products usually in the preferred embodiment range from the 5 to 50 percent by weight, and most often range from about 10 to about 30 percent by weight. Generally, polymethylene polyphenylpolyamines have an average functionality of from about 2.1 to about 3.0, more often 2.2-2.7.

According to another embodiment, the invention also relates to a process for preparing di- and polyisocyanates by conversion of the diamines and/or polyamines produced by means of the present invention. Subsequent conversion of the diamines and/or polyamines, produced by means of the present invention, to the corresponding isocyanates, by any of the many and varied prior art processes, results in diisocyanates and/or polymeric isocyanates with improved color and lower contents of chlorine-containing impurities in an economically beneficial way compared to the isocyanates produced from conventional polymethylene polyphenyl polyamines.

DETAILED DESCRIPTION

An improved method of preparing diaminodiphenylmethane and higher homologues thereof has now been discovered. The invention comprises the step of condensing aniline and formaldehyde either prior to addition of or in the presence of specific heterogeneous catalysts selected from the class of (a) delaminated zeolites and/or (b) metal silicate catalysts having an ordered mesoporous pore structure and/or (c) delaminated phyllosilicates. Subsequently, the resulting mixture is converted, in the presence of said catalyst(s), substantially to the desired mixture of aromatic primary amines.

A mixture of products is produced which includes the diaminodiphenylmethane isomers comprising the 2,2', 2,4', and 4,4' diamine isomers and higher homologues thereof or polymethylene polyphenylamines. The latter are higher molecular weight condensation polymers of the formaldehyde and the aniline and are considered homologues of the simple diaminodiphenylmethane isomers.

Depending upon reaction conditions, amount of catalyst employed, proportions of the reactants, and other variables the proportions of diamines, and higher polyamines present in the final reaction mixture may be widely varied. However, usually the reaction mixture contains at least 10 percent by weight of diamine with the remainder being higher polyamines thereof. More often, the percentage of diamines in the mixture is 50-95 percent and most often ranges from about 70 to about 90 weight percent. Correspondingly, the polymeric products higher than the diamine products usually in the preferred embodiment range from the 5 to 50 percent by weight, and most often range from about 10 to about 30 percent by weight. Generally, polymethylene polyphenylpolyamines have an average functionality of from about 2.1 to about 3.0, more often 2.2-2.7.

The specific heterogeneous catalysts of the present invention are selected from (a) delaminated zeolites and/or (b) metal silicate catalysts having an ordered mesoporous pore structure and/or (c) delaminated phyllosilicates. Preferred catalysts within this class of catalysts are those referred to as under (a) ITQ-2, ITQ-6 and ITQ-18, under (b) MCM-41 and under (c) delaminated magadiite and delaminated kenyaite. ITQ-2 catalysts are described in detail in published articles Corma et al, Chem Commun, 1999, 779-780; A. Corma et al, Nature 396(1998) 353 and U.S. Pat. No. 6,231,751, which are incorporated by reference. ITQ-6 materials are fully described in WO00/07722, which is incorporated by reference. ITQ-18 materials are fully described in EP 1211224, which is incorporated by reference. MCM-41 are described in published articles J. S. Beck et al, J. Am. Chem. Soc. 114 (1992) 10834 and A. Corma, Chem Rev. 97 (1997) 2373, which are incorporated by reference. Delaminated magadiite and delaminated kenyaite are described by B. Zebib, J. Blanchard and F-F Lambert in the Proceedings of 13$^{th}$ International Congress on Catalysis, Paris 2004, which is incorporated by reference.

Metal silicate catalysts having ordered mesoporous pore structure consist of an inorganic oxide porous substance and have a pore diameter of 1.5 to 30 nm, which is larger than known zeolite pore diameters. The pore size distribution is generally uniform and the pores are regularly arranged. The pore structure of such mesoporous materials is large enough to absorb large molecules, and the pore wall structure can be as thin as about 1 nm. Further, such mesoporous materials are known to have large specific surface areas (about 1000 m.sup.2/g) and large pore volumes (about 1 cc/g).

Examples of such mesoporous materials are FSM-16 (T. Yanagisawa et al., Bull. Chem. Soc. Jpn., 63,988 (1990), S. Inagaki et al., J. Chem. Soc., Chem. Commun., 680 (1993)) and the M41S's (e.g., MCM-41, MCM-48) (C. T. Kresge et al., Nature, 359,710 (1992), J. S. Beck et al., J. Am. Chem. Soc., 114, 10834 (1992)), which references are all incorporated by reference.

The preferred MCM-41 type aluminosilicates having a narrow pore size distribution have been described by Kresge et al. in Nature 359 (1992), 710-712.

Aluminosilicate catalysts having ordered mesoporous pore structure have been disclosed in U.S. Pat. Nos. 5,098, 684 and 5,102,643, which are incorporated by reference. Depending on preparation conditions, M41S materials with hexagonal (MCM-41), cubic (MCM-48) or layered crystallographic structure have been disclosed (Beck et al., J. Am. Chem. Soc., vol. 114, 10834-10843 (1992)).

Preferred silicates of MCM-41 structure are: amorphous mesoporous MCM-41 having an adjustable pore width in the range of typically 3 to 10 nm (see, for example, J. Am. Chem. Soc. 114 (1992) 10834-10843, U.S. Pat. No. 5,098, 684, U.S. Pat. No. 5,105,051, U.S. Pat. No. 5,134,242, and U.S. Pat. No. 5,134,243), molecular sieves of the M41S family, such as MCM-41 of hexagonal structure, MCM-50 of laminar structure (see Stud. Surf. Sci. Catal. 84 (1994) 53-60), MCM-48 of cubic structure (see Stud. Surf. Sci. Catal. 84 (1994) 53-60), FSM-16 (see Stud. Surf. Sci. Catal. 84 (1994) 125-132), metal silicates having different metals M (see WO 91/11390 for M=Al, J. Chem. Soc., Chem. Commun. (1994) 147-148 for M=Ti, J. Chem. Soc., Chem. Commun. (1994) 1059-1060 for M=V, and Prep. 6th Int. Symp. Sci. Bases Heterog. Cat. 1 (1994) 345-352 for M=W, Mo, Pb and Fe).

The amount of catalyst used here may be varied according to the choice of the experimenter. Usually, up to 30 percent by weight of catalyst based on weight on formaldehyde condensate is employed.

In order to prepare the methylene-bridged polyphenyl polyamines (term includes both diaminodiphenylmethane isomers and higher homologues thereof or higher polymers) the following process conditions are preferred.

The molar ratio of aniline to formaldehyde may be varied within comparatively wide limits. Thus, for example, from about 1 to about 15 mols of aniline may be employed per mol of formaldehyde. In general, at the lower aniline: formaldehyde ratios, such as ratios of from about 1 to about 5, the higher polymers will be formed preferentially and the yield of higher polymers is in excess of the yield of dimer. However, as progressively larger amounts of aniline are used, the yield of dimer is progressively increased at the expense of polymer yield.

As indicated above, the dimer will be formed as a mixture of the 2,2'-, 2,4'- and 4,4'-diamine isomers.

Formaldehyde may be employed in any of its commercially available forms. Thus, formalin, paraformaldehyde, "stabilized" methanol solutions of formaldehyde, gas etc., may be employed.

The reaction may be conducted in the presence or absence of an organic solvent. When a solvent is to be employed, it may be any suitable solvent selected from amongst the conventionally known aromatic or aliphatic solvents such as hydrocarbon solvents or chlorinated hydrocarbons, alcohols, ethers, esters, etc. boiling within the range from about 50° C. to about 250° C. The solvent should be employed in an amount sufficient to provide a single phase solution of the amine compound. Water may also be present with the catalyst of the present invention, which is an additional benefit towards prior art catalysts.

The reaction conditions to be employed may suitably include a reaction temperature within the range of about 50° C. to about 250° C., and more preferably within the range of about 50° C. to about 150° C.

Pressure is not particularly critical with respect to the process. However, the pressure should be sufficient to provide for liquid phase reaction conditions. Thus, pressures ranging from atmospheric up to 1000 psig may be employed.

The reaction may be carried out batch-wise, semi-continuously or continuously. Both slurry phase and fixed bed reactors may be employed. The form of the catalyst particles may be varied according to the preferred reactor configuration, and may include powders, micro-spheroidal particles, granules, extrudates, pellets, etc. The reaction may also be carried out using one or more reactor and catalyst types in combination. Many variations in reaction temperatures and times may be employed to enhance the application of the invention.

The diamines and polyaminopolyphenylmethanes of the present invention are recovered from the reaction mixture by any desired means. When the reaction is carried out with the catalyst dispersed in a slurry, the products are conveniently recovered by filtering the catalyst and removing water and excess aniline by distillation under reduced pressure. The bottoms from these operations will consist of diamine and polyamine in proportions depending on the ratio of aniline to formaldehyde, as indicated above. If it is desired to separate the diamine from the polyamine, this is easily accomplished by simple distillation or any suitable means.

The diamine and higher products such as triamines, tetramines and oligomers are useful for a variety of purposes. For example, they may be utilized as raw materials for the production of the corresponding di- and polyisocyanates. They may also be used in the production of polyols, formed via the polymerization reaction of the diamine and polyamines products of this invention with ethylene oxide and/or propylene oxide.

The advantages in using the specific catalysts of the present invention in the process of the invention are many and varied. In the first place, a more substantially rearranged product to primary amines is achieved in a desirable manner, compared to many prior art heterogeneous catalysts used in this process. In addition, many commonly used catalysts such as hydrochloric acid are highly corrosive, whereas there is no indication here that the catalysts used here are corrosive in any manner.

Surprisingly, it has been found that the specific catalysts of the present invention exhibit high activity with selectivity towards 4,4'-diamine comparable to the selectivity obtained from heterogeneous catalyst processes. Preferred catalysts are ITQ-2, ITQ-18, ITQ-6 and MCM-41. In case of the preferred ITQ-18 and MCM-41 catalysts, the selectivity to 4,4'-diamine is even higher. Preferred combination of catalyst are ITQ-2 or ITQ-6 either in combination with ITQ-18 and/or MCM-41.

According to another embodiment of the present invention, the present invention also relates to a process for preparing di- and polyisocyanates by conversion of the diamines and/or polyamines produced by means of the present invention.

Subsequent conversion of the diamines and/or polyamines, produced by means of the present invention, to the corresponding isocyanates, by any of the many and varied prior art processes, results in diisocyanates and/or polymeric isocyanates with improved colour and lower contents of chlorine-containing impurities in an economically beneficial way compared to the isocyanates produced from conventional polymethylene polyphenyl polyamines.

The above benefits can be obtained with even small amounts of catalyst employed, and the catalyst is readily removed from the reaction mixture by e.g. filtration.

The following examples illustrate the process of the invention. It is understood, of course, that these examples are merely illustrative, and that the invention is not to be limited thereto.

EXAMPLES

Example 1

ITQ-2 was synthesized in the laboratory according to reported preparations. The catalyst was calcined in air at 540° C. for 6 hours before using.

Reaction Procedure and Product Characterisation.

Synthesis of the Neutral Condensate

In a 100 ml three-necked flask 50.00 g of aniline was added and heated at autogeneous pressure in an oil bath at 50° C., with stirring. Formaldehyde (37 wt % aqueous solution) was added from a Cole-Parmer 74900 series syringe pump at 1.000 g min$^{-1}$ for 15 min. The aniline-formaldehyde (A/F) molar ratio was 2.9. After complete condensation, water and methanol were distilled in a rotavapor for 1 hour at 50° C. and 100 torr. A small quantity of aniline was lost in the distillation step (about 2-3 wt %). Thus, after water removal, aniline was added to the mixture in order to come back to the original A/F ratio. The distillation was carried out just until 5 wt % of water was left.

Isomerisation of the Mixture into Primary Amines 4.00 g of the A/F mixture was introduced in a 25 ml flask, with a reflux condenser, a nitrogen inlet and nitrobenzene as internal standard (15 mg g$^{-1}$). The mixture was heated to 150° C. and then 1.00 g of the catalyst was introduced. The reaction was left for 60-120 min. After reaction a $\frac{1}{10}$ dilution of the crude was prepared with methanol, and filtered to remove the catalyst. This sample was analysed by gas chromatography (GC). $^1$H-NMR characterization of the crude was also carried out.

Results and Discussion

Condensation and isomerisation of aniline with formaldehyde over ITQ-2 yielded a mixture of diamines and triamines preferentially. Working at 150° C., with a A/F ratio=2.9 (M) and a catalyst charge of 20 wt %, an amine content about 98-99 wt % was present in the crude after 0.5-1 hour. Total amounts of intermediates such as secondary amines and quinazolines, as well as impurities like N-methylated compounds, were about 1 wt %. No higher polyamines than tri-amines were found in the final crude.

Example 2

MCM-41 was prepared in the laboratory according to reported procedures.

Reaction Procedure and Product Characterisation

Synthesis of the Neutral Condensate

In a 100 ml three-necked flask 49.90 g of aniline was introduced and heated at autogeneous pressure in an oil bath at 50° C., with stirring. Formaldehyde (37 wt % aqueous solution) was added with a Cole-Parmer 74900 series syringe pump at 1.000 g min$^{-1}$ for 15 min. The A/F molar ratio was 2.90. After addition of formaldehyde the mixture was left stirring for 45 min, in order to complete the condensation. After condensation, water and methanol were distilled in a rotavapor for 1 hour at 60° C. and 100 torr. A small quantity of aniline was lost in the distillation step (1.593 g). Thus, after water removal, aniline was added to the mixture in order to come back to the original A/F ratio.

Isomerisation of the Mixture into Primary Amines 4.000 g of the A/F mixture, 0.075 g of nitrobenzene (internal standard, ALDRICH) and 0.750-0.950 g (15-19 wt %) of catalyst were introduced in a 25 ml flask, with a reflux condenser and nitrogen inlet. 0.210 g of milli-Q water was added in order to obtain a 5 wt % water content in the reactant mixture. The mixture was heated at 150° C. Then, the reaction was left for 60-120 min. Reaction was stopped by cooling the mixture in an ice bath. Then, 20 ml of methanol was added to the cooled crude. This dilution was filtered and analyzed directly by GC. After this, methanol was completely removed from the mixture in a rotavapor (15 min, 40° C., 100 torr). This crude, free of methanol, was also characterized by $^1$H-NMR.

Results and Discussion

Condensation and isomerisation of aniline with formaldehyde over MCM-41 yielded a mixture of diamines and triamines preferentially. Working at 150° C., with a A/F ratio=2.9 (M) and a catalyst charge of 19 wt %, an amine content about 98-99 wt % was present in the crude after 1-2 hours. Total amounts of intermediates such as secondary amines and quinazolines, as well as impurities like N-methylated compounds, were about 1 wt %. No higher polyamines than tri-amines were found in the final crude. Compared with Example 1, the levels of the 2,4' diamine isomer found in the final product mixture were significantly reduced.

Example 3

ITQ-6 was prepared in the laboratory according to reported procedures.

Reaction Procedure and Product Characterisation

Synthesis of the Neutral Condensate

In a 100 ml three-necked flask 49.90 g of aniline was introduced and heated at autogeneous pressure in an oil bath at 50° C., with stirring. Formaldehyde (37 wt % aqueous solution) was added with a Cole-Parmer 74900 series syringe pump at 1.000 g min$^{-1}$ for 15 min. The A/F molar ratio was 2.90. After addition of formaldehyde the mixture was left stirring for 45 minutes, in order to complete the condensation process. After condensation, water and methanol were distilled in a rotavapor for 1 hour at 60° C. and 100 torr. A small quantity of aniline was lost in the distillation step (1.593 g). Thus, after water removal, aniline was added to the mixture in order to come back to the original A/F ratio.

Isomerisation of the Mixture into Primary Amines 4.000 g of the A/F mixture, 0.075 g of nitrobenzene (internal standard, ALDRICH) and 0.750-0.950 g (15-19 wt %) of catalyst were introduced in a 25 ml flask, with a reflux condenser and nitrogen inlet. 0.210 g of milli-Q water was added in order to obtain a 5 wt % water content in the reactant mixture. The mixture was heated at 150° C. Then, the reaction was left for 60-120 min. Reaction was stopped by cooling the mixture in an ice bath. Then, 20 ml of methanol was added to the cooled crude. This dilution was filtered and analyzed directly by GC. After this, methanol was completely removed from the mixture in a rotavapor (15 min, 40° C., 100 torr). This crude, free of methanol, was also characterized by $^1$H-NMR.

Results and Discussion

Condensation and isomerisation of aniline with formaldehyde over ITQ-6 yielded a mixture of diamines and triamines preferentially. Working at 150° C., with a A/F ratio=2.9 (M) and a catalyst charge of 15-18 wt %, an amine content about 97-99 wt % was present in the crude after 1-2 hours. Total amounts of intermediates such as secondary amines and quinazolines, as well as impurities like N-methylated compounds, were about 1 wt %. No higher polyamines than tri-amines were found in the final crude. The levels of the 2,4' diamine isomer found in the final product mixture were similar to that found in Example 1.

Example 4

ITQ-18 was prepared in the laboratory according to reported procedures.

Reaction Procedure and Product Characterisation

Synthesis of the Neutral Condensate

In a 100 ml three-necked flask 49.90 g of aniline was introduced and heated at autogeneous pressure in an oil bath at 50° C., with stirring. Formaldehyde (37 wt % aqueous solution) was added with a Cole-Parmer 74900 series syringe pump at 1.000 g min$^{-1}$ for 15 min. The A/F molar ratio was 2.90. After addition of formaldehyde the mixture was left stirring for 45 minutes. After condensation, water and methanol were distilled in a rotavapor for 1 hour at 60° C. and 100 torr. A small quantity of aniline was lost in the distillation step (1-2 g). Thus, after water removal, aniline was added to the mixture in order to come back to the original A/F ratio.

Isomerization of the Mixture into Primary Amines 4.000 g of the A/F mixture, 0.075 g of nitrobenzene (internal standard, ALDRICH) and 1.28 g (24 wt %) of catalyst were introduced in a 25 ml flask, with a reflux condenser and nitrogen inlet. The mixture was heated at 160° C. Then, the reaction was left for 60 min. Reaction was stopped by cooling the mixture in an ice bath. Then, 20 ml of methanol was added to the cooled crude. This dilution was filtered and analyzed directly by GC. After this, methanol was completely removed from the mixture in a rotavapor (15 min, 40° C., 100 torr). This crude, free of methanol, was also characterized by $^1$H-NMR.

Results and Discussion

Condensation and isomerisation of aniline with formaldehyde over ITQ-18 yielded a mixture of diamines and triamines preferentially. Working at 150° C., with a A/F ratio=2.9 (M) and a catalyst charge of 24 wt %, an amine content about 99-100 wt % was present in the crude after 1 hour. Total amounts of intermediates such secondary amines and quinazolines, as well as impurities like N-methylated compounds, were less than 1 wt %. No higher polyamines than tri-amines were found in the final crude. Compared with Example 1, the levels of the 2,4' diamine isomer found in the final product mixture were significantly lower.

Example 5

Delaminated Al-Magadiite was prepared according to the following procedure.

0.350 g sodium aluminate (Carlo Erba, 32.8% Na$_2$O, 54% Al$_2$O$_3$) were diluted in a basic solution of 1.44 g NaOH (Scharlau 100%) and 35.4 g H$_2$O (milli Q), to obtain a clear solution. Then 37.5 g Ludox AS-40 (Aldrich, suspension in water 40%) were added and the mixture kept under stirring for 2 hours. The final gel was loaded in Teflon lined stainless steel autoclaves and heated at 150° C. for 4 days with continuous agitation. The resulting product Al-Magadiite was filtered off, washed until neutral pH was obtained and dried at 100° C. The molar composition of this gel is: SiO$_2$:0.2 NaOH:15H$_2$O:0.01 Al$_2$O$_3$.

A mixture of 2 g Al-Magadiite, 8 g H$_2$O (milli Q), 40 g CTMA-OH/Br (40%) and 12 g TPA-OH/Br (30%) was held at reflux at 80° C. for 16 hours. The swollen Magadiite was dispersed in 250 ml of H$_2$O (milli Q) and treated in a ultrasound bath for 1 hour. Then the suspension was acidified with HCl (4M) to pH=2. The product obtained was centrifuged at 12000 rpm and the recovered solids were washed with $H_2O$ (milli Q) until neutral pH was obtained, and dried at 100° C. overnight. Then, the delaminated solid was calcined at 450 degrees C. for 6 hours before use.

Reaction Procedure and Product Characterisation.

Synthesis of the Neutral Condensate

In a 100 ml three-necked flask 50.00 g of aniline was added and heated at autogeneous pressure in an oil bath at 50° C., with stirring. Formaldehyde (37 wt % aqueous solution) was added from a Cole-Parmer 74900 series syringe pump at 1.000 g $min^{-1}$ for 15 min. The aniline-formaldehyde (A/F) molar ratio was 2.9. After complete condensation, water and methanol were distilled in a rotavapor for 1 hour at 50° C. and 100 torr. A small quantity of aniline was lost in the distillation step (about 2-3 wt %). Thus, after water removal, aniline was added to the mixture in order to come back to the original A/F ratio. The distillation was carried out just until 5 wt % of water was left.

Isomerisation of the Mixture into Primary Amines 4.00 g of the A/F mixture was introduced in a 25 ml flask, with a reflux condenser, a nitrogen inlet and nitrobenzene as internal standard (15 mg $g^{-1}$). The mixture was heated to 150° C. and then 1.00 g of the catalyst was introduced. The reaction was left for 240 min. After reaction a 1/10 dilution of the crude was prepared with methanol, and filtered to remove the catalyst. This sample was analysed by GC. $^1$H-NMR characterization of the crude was also carried out.

Results and Discussion

Condensation and isomerisation of aniline with formaldehyde over delaminated magadiite yielded a mixture of diamines and triamines preferentially. Working at 150° C., with a A/F ratio=2.9 (M) and a catalyst charge of 20 wt %, an amine content about 98-99 wt % was present in the crude after 4 hours. Total amounts of intermediates such as secondary amines and quinazolines, as well as impurities like N-methylated compounds, were about 1 wt %. No higher polyamines than tri-amines were found in the final crude.

What is claimed is:

1. A method of preparing diaminodiphenylmethane and higher homologues thereof comprising the step of condensing aniline and formaldehyde in the presence of a heterogeneous solid acid catalyst selected from the group consisting of delaminated zeolites, metal silicate catalysts having an ordered mesoporous pore structure, delaminated phyllosilicates, and mixtures thereof.

2. The method according to claim 1 whereby the catalyst is selected from the group consisting of ITQ-2, ITQ-6, ITQ-18, MCM-41, delaminated magadiite and delaminated kenyaite.

3. A method of preparing polyisocyanates comprising the steps of:
   (a) condensing aniline and formaldehyde either prior to the addition of or in the presence of a heterogeneous solid acid catalyst selected from the group consisting of delaminated zeolites, metal silicate catalysts having an ordered mesoporous pore structure, delaminated phyllosilicates, and mixtures thereof to produce diaminodiphenylmethane and higher homologues thereof, and
   (b) converting the diaminodiphenylmethane and higher homologues thereof, in the presence of the heterogeneous solid acid catalyst, to corresponding polyisocyanates.

4. The method according to claim 3 whereby the catalyst is selected from the group consisting of ITQ-2, ITQ-6, ITQ-18, MCM-41, delaminated magadiite and delaminated kenyaite.

* * * * *